(12) United States Patent
Mitsui et al.

(10) Patent No.: US 7,227,051 B2
(45) Date of Patent: Jun. 5, 2007

(54) DISPOSABLE WEARING ARTICLE

(75) Inventors: Koichiro Mitsui, Kagawa-ken (JP);
Masakazu Shiraishi, Kagawa-ken (JP);
Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 121 days.

(21) Appl. No.: 10/736,494

(22) Filed: Dec. 17, 2003

(65) Prior Publication Data
US 2004/0127865 A1 Jul. 1, 2004

(30) Foreign Application Priority Data
Dec. 20, 2002 (JP) .............................. 2002-371036

(51) Int. Cl.
*A61F 13/15* (2006.01)
*B32B 7/14* (2006.01)
(52) U.S. Cl. ....................... 604/366; 428/198; 156/291
(58) Field of Classification Search ................ 604/358, 604/365, 385.23, 366; 156/291, 204, 227; 239/417; 428/195.1, 198, 196; 493/131
See application file for complete search history.

(56) References Cited

U.S. PATENT DOCUMENTS

| | | | | |
|---|---|---|---|---|
| 2,705,498 | A | * | 4/1955 | Johnson ....................... 604/365 |
| 2,734,843 | A | * | 2/1956 | Steele ......................... 156/197 |
| 3,677,249 | A | * | 7/1972 | Kokx .......................... 604/366 |
| 3,682,755 | A | * | 8/1972 | Lee ............................. 428/108 |
| 3,727,615 | A | * | 4/1973 | Duchane ....................... 604/365 |
| 3,730,798 | A | * | 5/1973 | Franz .......................... 156/201 |
| 4,050,462 | A | * | 9/1977 | Woon et al. .................. 604/365 |
| 4,081,301 | A | * | 3/1978 | Buell ........................... 156/164 |
| 4,488,923 | A | * | 12/1984 | Pieniak ........................ 156/199 |
| 4,573,986 | A | * | 3/1986 | Minetola et al. ............. 604/366 |
| 4,849,049 | A | * | 7/1989 | Colton ........................ 156/291 |
| 4,874,451 | A | * | 10/1989 | Boger et al. ................. 156/291 |
| 4,880,420 | A | * | 11/1989 | Pomparelli ............. 604/385.27 |
| 4,891,258 | A | * | 1/1990 | Fahrenkrug .................. 428/138 |
| 4,894,277 | A | * | 1/1990 | Akasaki ....................... 428/198 |
| 4,960,619 | A | * | 10/1990 | Slautterback et al. ....... 427/265 |
| 5,024,667 | A | * | 6/1991 | Malcolm et al. ............. 604/382 |
| 5,107,866 | A | * | 4/1992 | Aronoff et al. ............. 131/365 |
| 5,330,598 | A | * | 7/1994 | Erdman et al. ............. 156/164 |
| 5,354,597 | A | * | 10/1994 | Capik et al. ................. 428/152 |

(Continued)

FOREIGN PATENT DOCUMENTS

JP          2001-95837          4/2001

*Primary Examiner*—Tatyana Zalukaeva
*Assistant Examiner*—Paula L. Craig
(74) *Attorney, Agent, or Firm*—Lowe Hauptman & Berner, LLP

(57) ABSTRACT

A disposable wearing article includes a liquid-pervious topsheet, a liquid-impervious backsheet, a liquid-absorbent core interposed between the top- and backsheets, a pair of liquid-impervious leak-barrier sheets and a pair of elastically stretchable sheets. Each portion of the aforesaid sheets placed one upon another are joined together by means of adhesives and the core is joined to inner surfaces of the top- and backsheets by means of adhesives. Adhesives are defined by a plurality of adhesive lines continuously extending in a given direction and each of the adhesive lines includes first and second zones arranged alternately in the given direction along the adhesive line. A quantity of adhesives in the first zone is much more than a quantity of adhesives in the second zone.

4 Claims, 10 Drawing Sheets

U.S. PATENT DOCUMENTS

| | | | |
|---|---|---|---|
| 5,421,921 A * | 6/1995 | Gill et al. | 156/62.4 |
| 5,569,231 A * | 10/1996 | Emenaker et al. | 604/385.23 |
| 5,593,400 A * | 1/1997 | O'Leary | 604/385.27 |
| 5,643,384 A * | 7/1997 | Okabe | 156/206 |
| 5,688,218 A * | 11/1997 | Jenkins | 493/151 |
| 5,800,867 A * | 9/1998 | Matsunaga et al. | 427/476 |
| 5,868,725 A * | 2/1999 | Coles et al. | 604/385.23 |
| 5,882,573 A * | 3/1999 | Kwok et al. | 264/510 |
| 5,942,062 A * | 8/1999 | Hassall et al. | 156/87 |
| 5,984,911 A * | 11/1999 | Siebers et al. | 604/391 |
| 6,120,487 A * | 9/2000 | Ashton | 604/385.29 |
| H1978 H * | 8/2001 | Freiburger et al. | 156/78 |
| 6,325,786 B1 * | 12/2001 | Bjorklund et al. | 604/385.01 |
| 6,417,122 B1 * | 7/2002 | Newkirk et al. | 442/364 |
| 6,436,083 B1 * | 8/2002 | Mishima et al. | 604/385.24 |
| 6,461,430 B1 * | 10/2002 | Kwok | 118/325 |
| 6,602,238 B2 * | 8/2003 | Takei et al. | 604/385.26 |
| 6,602,554 B1 * | 8/2003 | Kwok | 427/424 |
| 6,635,798 B1 * | 10/2003 | Yoshioka et al. | 604/365 |
| 2003/0045845 A1 * | 3/2003 | Yoshioka | 604/361 |
| 2003/0173018 A1 * | 9/2003 | Harris | 156/167 |

* cited by examiner

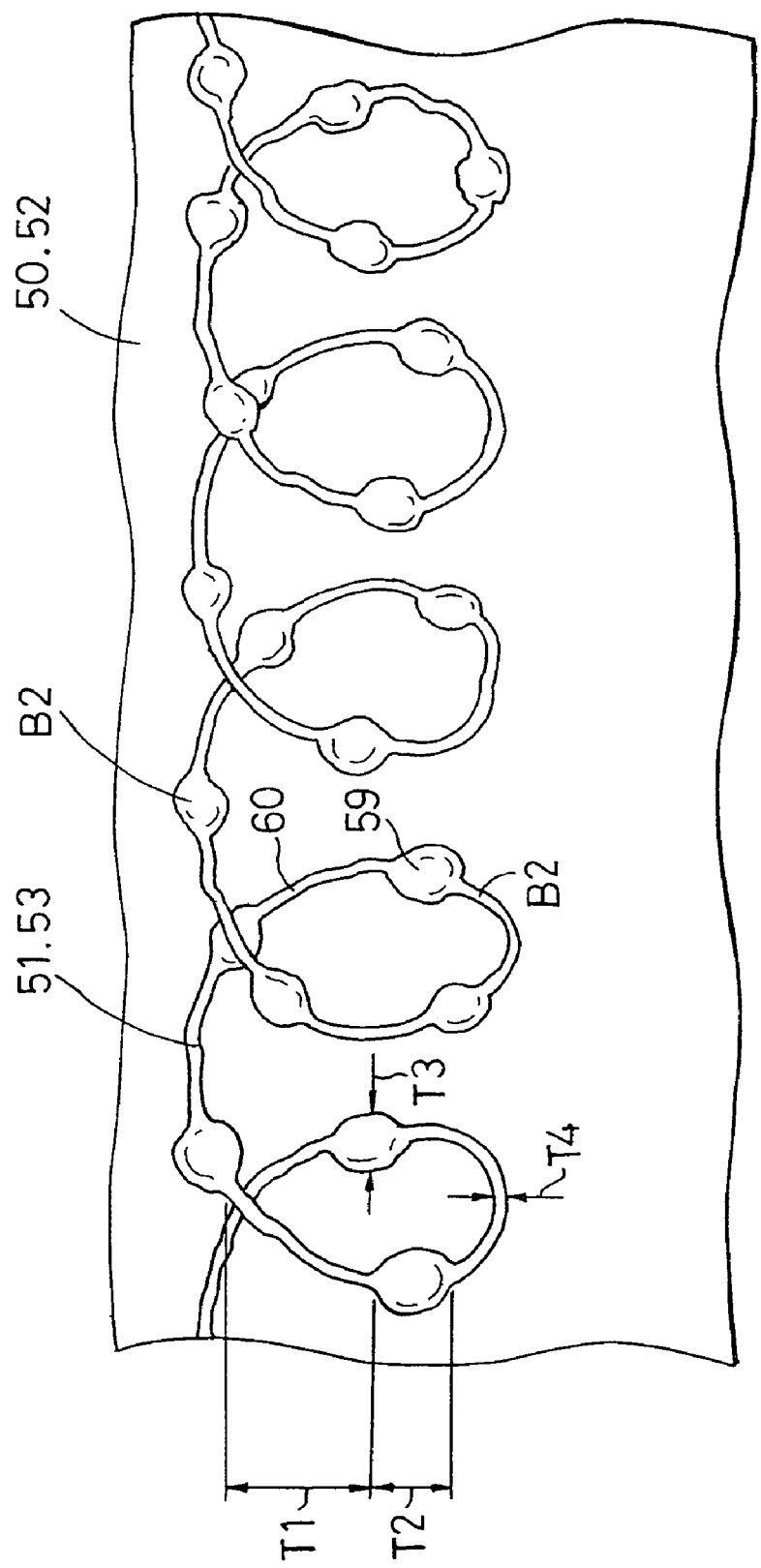

DISPOSABLE WEARING ARTICLE

RELATED APPLICATIONS

The present application is based on, and claims priority from, Japanese Application Serial Number 2002-371036, filed Dec. 20, 2002, the disclosure of which is hereby incorporated by reference herein in its entirety.

BACKGROUND OF THE INVENTION

The present invention generally relates to disposable wearing articles adapted to absorb and to contain bodily fluids such as sanitary napkin, urine pad or mother's milk pad.

A disposable diaper disclosed in Japanese Patent Application Publication No. 2001-95837A comprise a liquid-pervious topsheet lying on the side facing a wearer's body, a liquid-impervious backsheet lying on the side facing away from a wearer's body, an absorbent core interposed between these top- and backsheets and a pair of liquid-impervious leak-barrier sheets normally biased to rise on the core so as to define, as viewed in a longitudinal direction, front and rear waist regions, a crotch region extending between the waist regions, a pair of end flaps extending in a transverse direction outside longitudinally opposite ends of the core and a pair of side flaps extending in the longitudinal direction outside transversely opposite side edges of the core wherein the core is wrapped with tissue paper. In the known diaper, hot melt adhesives applied on the sheets and the tissue paper is used to join the top- and backsheets to each other, to join the leak-barrier sheets to the top- and backsheets, to join the tissue paper to the top- and backsheets and to join the core to the sheets and tissue paper.

In the diaper disclosed in the above-cited Publication, hot melt adhesives rather evenly applied on the sheets and the tissue paper forms a plurality of independent adhesive lines extending in the longitudinal direction, describing undulating curves. Of the adhesive lines, each pair of the adjacent adhesive lines are spaced apart from each other by a given distance in the transverse direction without intersecting each other while the individual adhesive lines intersect themselves in a few spots. Spread of adhesives on the sheets as well as on the tissue paper is in a range of 0.8 to 8 g/m².

According to the disclosure of the above-cited Publication, a plurality of independent adhesive lines extending in the longitudinal direction describing undulated curves allow the sheets, the tissue paper and the core to be joined one to another with a substantially equal adhesive strength in the longitudinal and transverse directions and thereby to prevent the components from unintentionally peeling off one from another. Furthermore, the spread of the adhesives in a range of 0.8 to 8 g/m² is effective to avoid an inconvenience that, even when a fibrous nonwoven fabric is used as a stock material for the topsheet, adhesives might clog fibrous interstices over a wide range and thereby to maintain a desired water-permeability of the topsheet.

In the case of the diaper disclosed in above-cited Publication, if the spread of adhesives on the sheets and the tissue paper is increased in order to reliably prevent the sheets, the tissue paper and the core from peeling off one from another, an excessive quantity of adhesives may seep into the fibrous interstices of the sheets and the tissue paper not only in the thickness direction but also in the planar direction. Consequently, cured adhesives may deteriorate a desired flexibility of the sheets. On the other hand, if the spread of adhesives on the sheets and the tissue paper is decreased in order to maintain the desired flexibility of the sheets, the adhesive strength required between the sheets, between the sheets and the tissue paper and between the core and the tissue paper may unacceptably reduced and the component may readily peel off one from another. For this diaper, adhesives rather evenly applied on the sheets and the tissue paper defines the adhesive lines, so the spread of adhesives can be adjusted merely by increasing or decreasing the spread of adhesives along the individual adhesive line as a whole. With a disadvantageous consequence, the adhesive strength required for the sheets, the tissue paper and the core is deteriorated and, if not, the flexibility of the sheets is deteriorated depending on the spread of adhesives. In this manner, it is difficult to ensure that the sheets, the tissue paper and the core are prevented from peeling off one from another and, at the same time, the flexibility of the sheets are maintained.

SUMMARY OF THE INVENTION

It is an object of the present invention to provide a disposable wearing article improved so as to reliably prevent an anxiety that the sheets might peel off from each other and/or the sheets and the core might peel off one from another while a desired flexibility of the sheets is maintained.

According to the present invention, there is provided an improvement in a disposable wearing article comprising at least a pair of sheets opposed to each other and a liquid-absorbent core interposed between the pair of sheets, and portions of said sheets which extend outward beyond a peripheral edge of the core in a circumferential direction being permanently joined to each other by means of adhesives and the core being permanently joined to at least one of the pair of sheets by means of adhesive.

The disposable wearing article further comprises the adhesives being defined by a plurality of adhesive lines applied on at least one of opposed surfaces of the pair of sheets and continuously extending in a given direction, each of the adhesive lines having first zones and second zones alternately arranged on the adhesive line so that each of the first zones contains much more quantity of the adhesives than each of the second zones contains.

The present invention may be exploited also in preferred manners as follow:

A quantity of adhesives per unit length of the first zone is in a range of 0.0001 to 0.0045 g/cm while a quantity of adhesives per unit length of the second zone is in a range of 0.00003 to 0.0008 g/cm and the quantity of the adhesives per unit length of the first zone is three or more times larger than the quantity of adhesives per unit length of the second zone.

The adhesive line is folded in three layers placed one upon another in a thickness direction of the article in the first zone.

A length of the first zone is in a range of 1 to 10 mm and a length of the second zone is in a range of 0.5 to 80 mm.

A width of the first zone is in a range of 0.01 to 3 mm while a width of the second zone is in a range of 0.003 to 0.5 mm and the width of the first zone is three or more times of the width of the second zone.

A spread of the adhesives on the pair of sheets is in a range of 2.0 to 100 g/m².

The core comprises a mixture of fluff pulp, super-absorbent polymer particles and thermoplastic synthetic resin fibers and at least a mixture of the pulp and the polymer particles and the adhesives are defined by the adhesive lines applied on the core and a spread of the adhesives applied on the core is in a range of 2.0 to 100 g/m².

At least one of the sheets is formed by at least one of a fibrous nonwoven fabric layer and a plastic film layer and the nonwoven fabric layer has a compressibility of 0.3 g·cm/m² or higher and a thickness of 0.2 mm or larger.

At least of the pair of sheets is formed from a composite sheet comprising an elastically stretchable plastic film and a fibrous nonwoven fabric laminated on at least one surface of the plastic film so that the film may be contractibly joined to the nonwoven fabric and the composite sheet may have a compressibility of 0.3 g·cm/m² or higher and a thickness of 0.2 mm or larger.

The wearing article comprises a disposable diaper composed of front and rear waist regions and a crotch region extending between the waist regions so as to be contoured by a pair of end flaps extending in a transverse direction outside longitudinally opposite ends of the core and a pair of side flaps extending in the longitudinal direction outside transversely opposite side edges of the core and, of a liquid-pervious topsheet lying on a side facing a wearer's skin, a liquid-impervious backsheet lying on a side facing away from a wearer's skin and liquid-impervious leak-barrier sheets extending in the longitudinal direction and normally biased to rise above the core, at least the top- and backsheets define the pair of sheets and, of the top- and backsheets and the leak-barrier sheets, at least the backsheet defines the end- and side flaps.

The wearing article comprises a sanitary napkin having front and rear regions, an intermediate region extending between the front and rear regions and end marginal zones extending in the transverse direction outside longitudinally opposite ends of the core and, lateral marginal zones extending in the longitudinal direction outside transversely opposite side edges of the core and, the pair of sheets are defined by a liquid-pervious topsheet lying on a side facing a wearer's body and a liquid-impervious backsheet lying on a side facing away from a wearer's skin and, of the top- and backsheets, at least the backsheet defines the end marginal zones as well as the lateral marginal zones.

BRIEF DESCRIPTION OF THE DRAWINGS

FIG. 11 is a partial overhead view depicting a nonwoven fabric and a film joining together by means of adhesives.

DETAILED DESCRIPTION OF THE PREFERRED EMBODIMENTS

Details of a disposable wearing article according to the present invention will be more fully understood from the description of a disposable diaper and a sanitary napkin, both embodiments of the invention, given hereunder in reference to the accompanying drawings.

Figure 1:
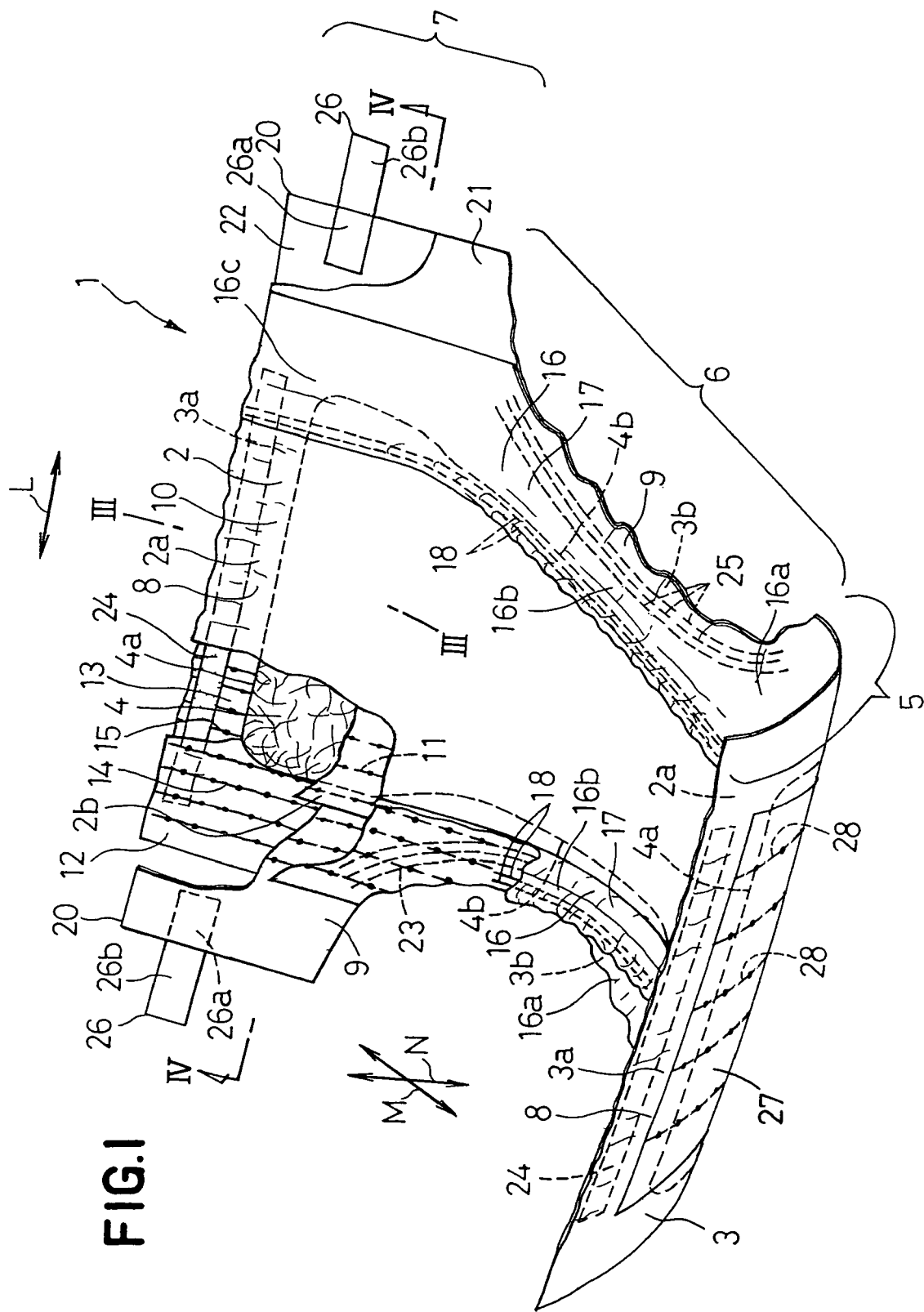
FIG. 1 is a partially cutaway perspective view of a disposable diaper as one embodiment of the invention.
Figure 2:
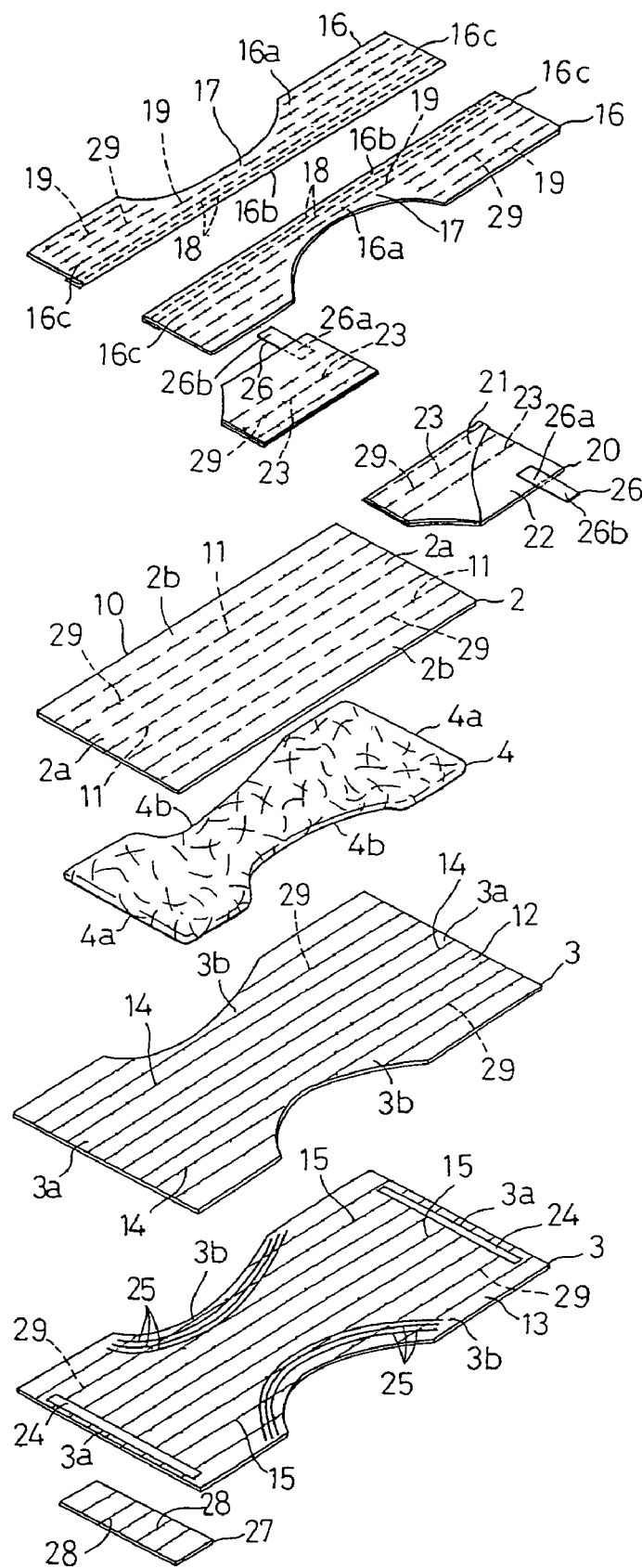
FIG. 2 is an exploded perspective view of the diaper depicted by FIG. 1.
Figure 3:
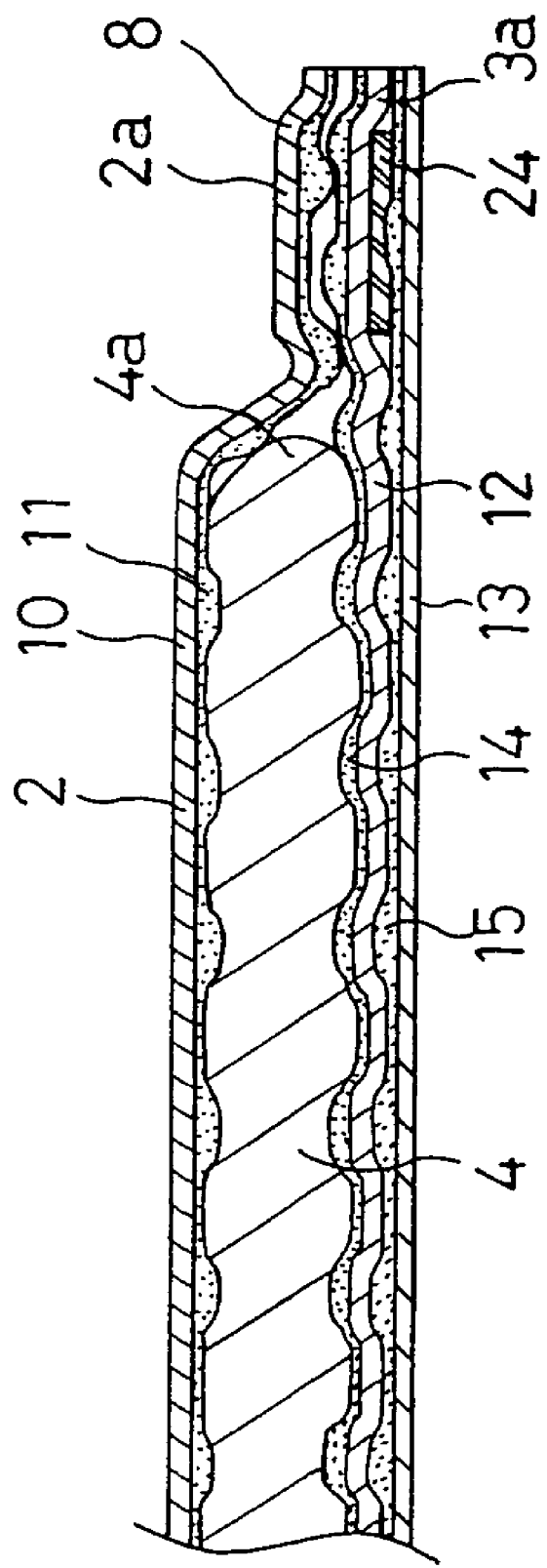
FIG. 3 is a sectional view taken along the line III—III in FIG. 1.
Figure 4:
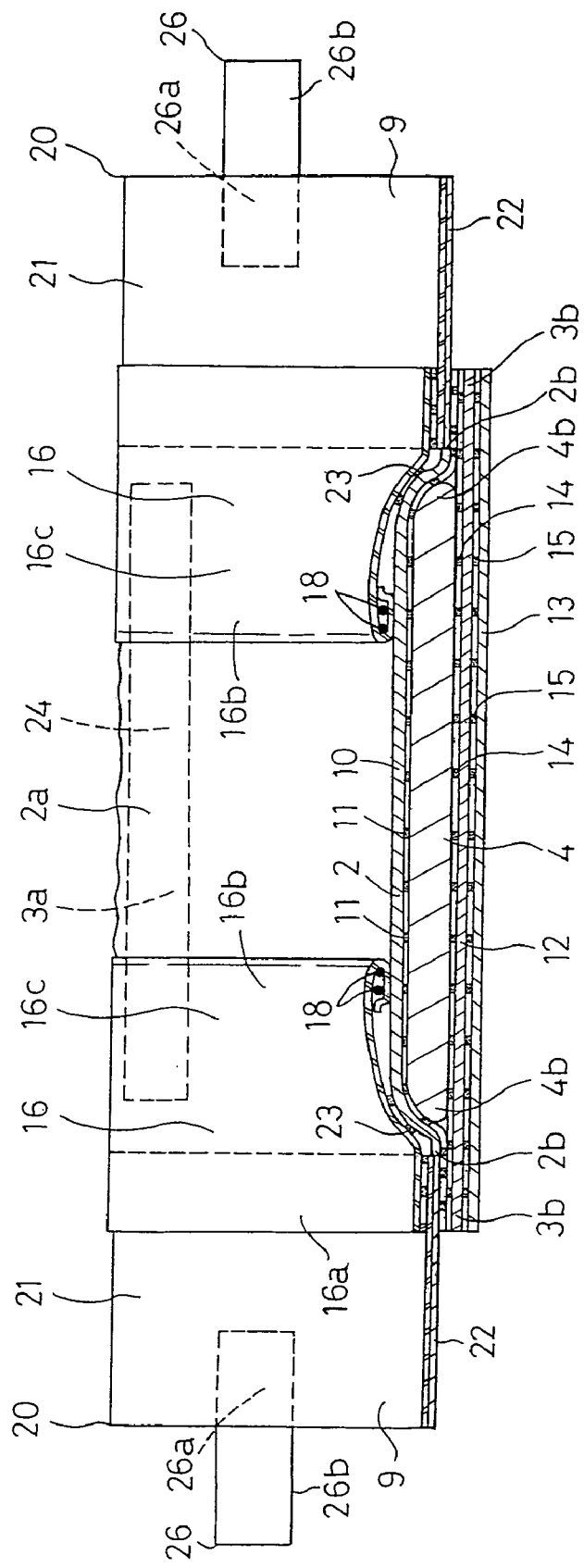
FIG. 4 is a sectional view taken along the line IV—IV with FIG. 1.

FIG. 1 is a partially cutaway perspective view depicting a disposable diaper 1 as a one embodiment of the invention, FIG. 2 is an exploded perspective view of the diaper 1 depicted by FIG. 1, FIG. 3 is a sectional view taken along the line III—III in FIG. 1 and FIG. 4 is a sectional view taken along the line IV—IV in FIG. 1. In FIG. 1, a transverse direction is indicated by an arrow L, a longitudinal direction is indicated by an arrow M and a thickness direction is indicated by an arrow N. FIG. 3 is, more specifically, a sectional view taken along a joining line 29. Expression used herein "inner surfaces" of nonwoven fabrics 10, 13, 17 and films 12, 22 refers to the surfaces facing a core 4 and expression "outer surfaces" thereof refers to the surfaces facing away from the core 4.

A diaper 1 basically comprises a liquid-pervious topsheet 2 lying on the skin-contactable side, a liquid-impervious backsheet 3 lying on the non-skin-contactable side, a liquid-absorbent core 4 interposed between the top- and backsheets 2, 3 and a pair of liquid-impervious leak-barrier sheets 16. In addition, the diaper 1 includes an elastically stretchable sheet 20, respective stretchable elastic members 18, 24, 25, tape fasteners 26 and a target tape strip 27. The diaper is composed of, as viewed in a longitudinal direction, a front waist region 5, a rear waist region 7 and a crotch region 6 extending between the two waist regions 5, 7. The diaper 1 further comprises a pair of end flaps 8 extending in a transverse direction outside longitudinally opposite ends 4a of the core 4 and a pair of side flaps 9 extending in the longitudinal direction outside transversely opposite side edges 4b of the core 4.

In the crotch region 6, the side flaps 9 describe circular arcs which are convex inward in the transverse direction of the diaper 1. The illustrated diaper 1 is of the so-called open-type with the front and rear waist regions 5, 7 adapted to be connected to each other immediately before put on a wearer's body and presenting a generally hourglass-like planar shape. The core 4 extends over the crotch region 6 further into the front and rear waist regions 5, 7 so as to occupy transversely middle zones thereof.

The topsheet 2 is formed from a hydrophilic fibrous nonwoven fabric 10 and having longitudinally opposite end zones 2a extending outward beyond the ends 4a of the core 4 in the longitudinal direction and transversely opposite lateral marginal zones 2b extending outward beyond the side edges 4b of the core 4. The nonwoven fabric 10 is coated on its inner surface with a plurality of adhesive lines 11 continuously extending in the longitudinal direction. The backsheet 3 is formed from a breathable liquid-impervious plastic film 12 and a hydrophobic fibrous nonwoven fabric 13 laid on the outer surface of the film 12. The backsheet 3 has longitudinally opposite end zones 3a extending in the longitudinal direction outward beyond the ends 4a of the core 4 and transversely opposite lateral marginal zones 3b extending in the transverse direction outward beyond the side edges 4b of the core 4. The film 12 is coated on its inner surface with a plurality of adhesive lines 14 continuously extending in the longitudinal direction. The nonwoven fabric 13 is coated on its inner surface with a plurality of adhesive lines 15 continuously extending in the longitudinal direction. The film 12 and the nonwoven fabric 13 have their inner and outer surfaces joined to each other by means of adhesives 15. Along the end zones 2a, 3a and the lateral marginal zones 2b, 3b of the top- and backsheet 2, 3, respectively, the inner surface of the nonwoven fabric 10 and the inner surface of the film 12 are joined to each other by means of adhesives 11, 14. The core 4 is joined to the inner surface of the nonwoven fabric 10 and to the inner surface of the film 12 by means of adhesives 11, 14, respectively.

The leak-barrier sheet 16 is formed from a hydrophobic fibrous nonwoven fabric 17 and extends along the associated side flap 9 in the longitudinal direction. The leak-barrier sheet 16 has a fixed lateral zone 16a extending in the longitudinal direction, a movable zone 16b extending in the longitudinal direction and normally biased to rise above the core 4 and fixed longitudinally opposite end zones 16c lying on the end flaps 8 and collapsed inward in the transverse direction of the diaper 1. The movable zone 16b is provided in the vicinity of its upper edge with a stretchable elastic member 18 extending in the longitudinal direction and contractibly bonded thereto. The elastic member 18 is joined to the movable zone 16b so that the elastic member 18 may be covered with a part of the movable zone 16b. In the fixed lateral zone 16a and the fixed longitudinally opposite end zones 16c, the nonwoven fabric 17 is coated on its inner surface with a plurality of adhesive lines 19 continuously extending in the longitudinal direction. In the fixed lateral zone 16a, the inner surface of the nonwoven fabric 17 is joined to the outer surface of the nonwoven fabric 10 and the inner surface of the film 12 by means of adhesives 14, 19. The nonwoven fabric 10 and the film 12 respectively define the top- and backsheets 2, 3. In the fixed longitudinally opposite end zones 16c, the inner surface of the nonwoven fabric 17 is joined to the outer surface of the nonwoven fabric 10 by means of adhesives 19. The elastic member 18 contracts as the diaper 1 curves in the longitudinal direction with the topsheet 2 inside and causes the movable zone 16b to rise above the core 41. The movable zone 16b rising in this manner forms a barrier against bodily discharges.

The elastically stretchable sheet 20 is laid in the rear waist region 7 and comprises a hydrophobic fibrous nonwoven fabric 21 and a breathable liquid-impervious elastically stretchable plastic film 22 laminated on the outer surface of the nonwoven fabric 21. In the elastically stretchable sheet 20, the nonwoven fabric 21 is joined to the film 22 while the latter is stretched at a predetermined ratio in the transverse direction so that the nonwoven fabric 21 is drawn inward in the transverse direction as the film 22 contract inward in the transverse direction and, in consequence, the sheet 20 is formed with a plurality of irregular gathers (not shown). The film 22 is partially coated with a plurality of adhesive lines 23 continuously extending in the longitudinal direction. The elastically stretchable sheet 20 is partially interposed between the lateral marginal zone 3b of the backsheet 3 and the fixed lateral zone 16a of the leak-barrier sheet 16. In the elastically stretchable sheet 20, the outer surface of the nonwoven fabric 21 is joined to the inner surface of the nonwoven fabric 17 defining the leak-barrier sheet 16 by means of adhesives 19 and the inner surface of the film 22 is joined to the inner surface of the film 12 defining the backsheet 3 by means of adhesives 14, 23.

The core 4 comprises a mixture of fluff pulp and super-absorbent polymer particles or a mixture of fluff pulp, super-absorbent polymer particles and thermoplastic synthetic resin fibers, in any case, compressed to a predetermined thickness. Optionally, the core 4 is entirely wrapped with liquid-pervious sheet such as a tissue paper or a hydrophilic fibrous nonwoven fabric to prevent the core 4 from getting out of its initial shape and/or to prevent the polymer particles from falling off.

The end flaps 8 are formed from the end zones 2a, 3a of the top- and backsheets 2, 3 extending outward beyond the ends 4a of the core 4 in the longitudinal direction and the fixed longitudinally opposite end zones 16c of the respective leak-barrier sheets 16. Each of the end flaps 8 is provided with a ribbon-like waist elastic member 24 contractibly joined thereto so as to extend in the transverse direction and to be contractible in this direction. The waist elastic member 24 is interposed between the film 12 and the nonwoven fabric 13 defining the backsheet 3 by means of adhesives 15.

The side flaps 9 are formed from the lateral marginal zones 2b, 3b of the top- and backsheets 2, 3, the fixed lateral zones 16a of the respective leak-barrier sheets 16 and the elastically stretchable sheets 20. The elastically stretchable sheet 20 forms a part of the side flap 9. In each of the side flaps 9, the lateral marginal zone 2b of the topsheet 2 extends outward slightly beyond the associated side edge 4b of the core 4 in the transverse direction and the lateral marginal zone 3b of the backsheet 3 as well as the fixed lateral zone 16a of the associated leak-barrier sheet 16 extend outward beyond the associated lateral zone 2b of the topsheet 2 in the transverse direction. The side flap 9 is provided with a plurality of leg elastic members 25 so as to extend in the longitudinal direction and to be contractible in this direction. The leg elastic members 25 are interposed between the film 12 and the nonwoven fabric 13 defining the backsheet 3 and joined to the film 12 and the nonwoven fabric 13 by means of adhesives 15.

Each of the tape fasteners 26 is formed from a flexible plastic film. The tape fastener 26 has a fixed end zone 26a and a free end zone 26b both extending in the transverse direction. The fixed end zone 26a is interposed between the film 21 and the nonwoven fabric 22 defining the elastically stretchable sheet 20 and joined thereto. The free end zone 26b is coated on its inner surface with pressure-sensitive adhesives (not shown) which is, in turn, covered with and protected by a release paper (not shown). The front waist region 5 is provided with the target tape strip 27 on which the free end zone 26b of the tape fastener 26 is detachably anchored. The target tape strip 27 is made of a flexible plastic film and has a rectangular shape which is relatively long in the transverse direction. The target tape strip 27 is coated with a plurality of adhesive lines 28 continuously extending in the longitudinal direction. The target tape strip 27 is joined to the outer surface of the nonwoven fabric 13 defining the backsheet 3 by means of adhesives 28.

To put the diaper 1 on a wearer, the side flaps 9 in the rear waist region 7 may be placed upon the outer surface of the side flaps 9 in the front waist region 5 and then the free end zones 26b of the respective tape fasteners 26 may be anchored on the target tape strip 27 by means of adhesives so as to connect the front and rear waist regions 5, 7 with each other. Upon connection of the front and rear waist regions 5, 7 with each other, the diaper 1 is formed with a waist-hole and a pair of leg-holes lying below the waist-hole (not shown).

Figure 5:
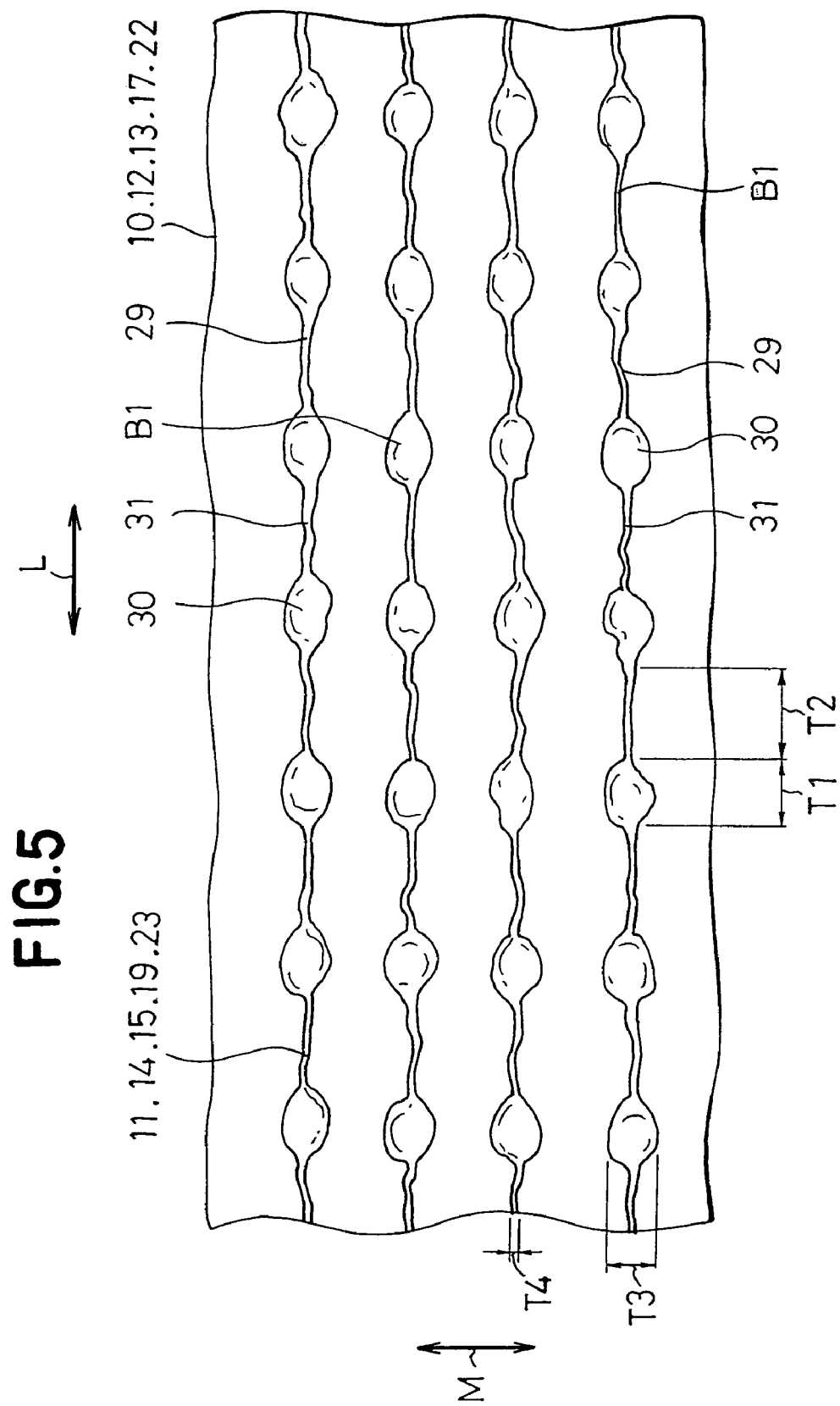
FIG. 5 is an overhead view depicting a nonwoven fabric or a film coated with adhesives.
Figure 6:
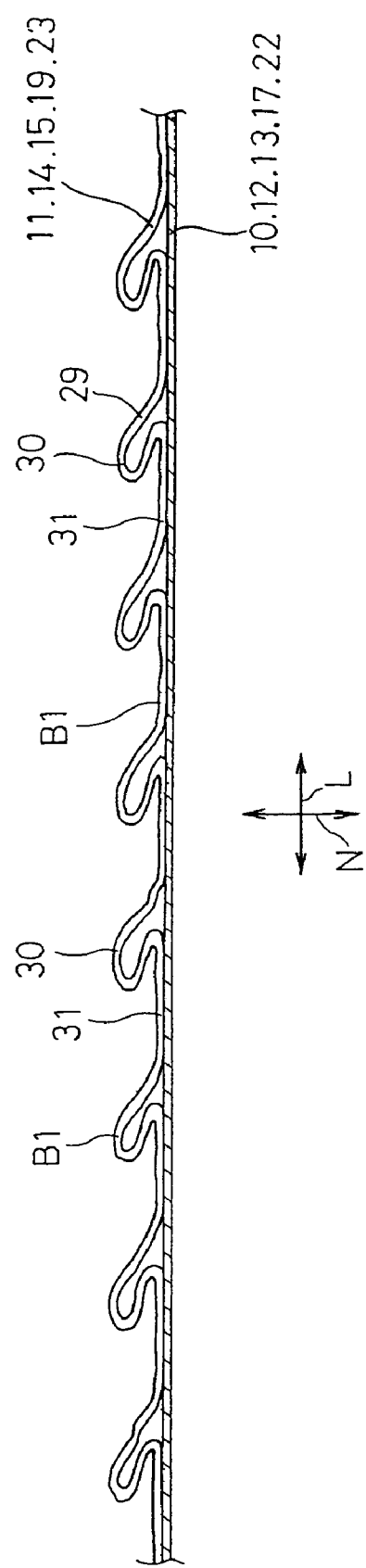
FIG. 6 is a diagram illustrating a manner in which the nonwoven fabric or the film is coated with adhesives.
Figure 7:
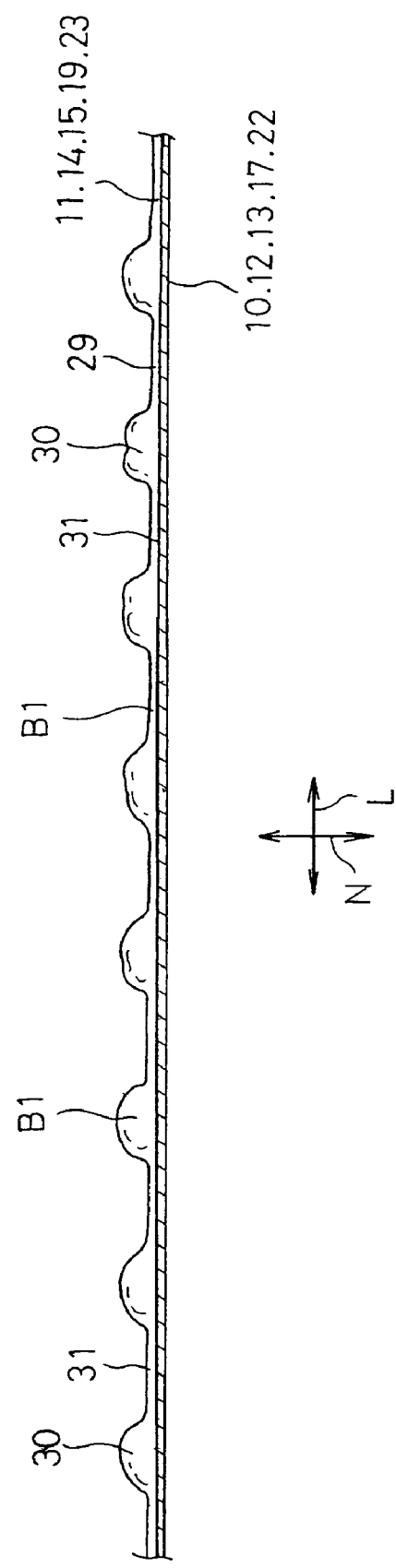
FIG. 7 is a diagram illustrating the nonwoven fabric or the film after coated with adhesives.

FIG. 5 is a partial overhead view depicting nonwoven fabrics 10, 13, 17 or films 12, 22 coated with adhesives 11, 14, 15, 19, 23, FIG. 6 is a diagram illustrating a manner in which the nonwoven fabrics 10, 13, 17 or the films 12, 22 is coated with adhesives 11, 14, 15, 19, 23 and FIG. 7 is a diagram illustrating the nonwoven fabrics 10, 13, 17 or the films 12, 22 after coated with adhesives 11, 14, 15, 19, 23. More specifically, FIG. 5 illustrates the state in which the nonwoven fabric layers 10, 17 have been joined together by means of adhesives 19 and then pressed in the thickness direction or the state in which the nonwoven fabric layers 10, 13 and the film layers 12, 22 joined together by means of adhesives 11, 14, 15, 23 have been pressed in the thickness direction. In FIGS. 5, 6 and 7, the longitudinal direction is indicated by an arrow L, the transverse direction is indicated by an arrow M (in FIG. 5 alone) and the thickness direction is indicated by an arrow N (only in FIGS. 6 and 7).

Adhesives 11, 14, 15, 19, 23 (hereinafter designated generically by B1) coated on the top- and backsheets 2, 3, the leak-barrier sheets 16, and the nonwoven fabric 10, 13, 17 and the films 12, 22 defining together the elastically stretchable sheet 20 is provided as a plurality of adhesive lines 29 which continuously extend in the longitudinal direction, describing substantially straight lines. Of the adhesive lines 29, each pair of the adjacent lines 29 do not intersect each other and are spaced apart from each other by a predetermined dimension in the transverse direction. The lines 29 comprise first zones 30 and second zones 31 arranged alternately in the longitudinal direction. As will be understood from FIG. 6, in each of the first zones 30, the adhesive line 29 forms three layers placed one upon another in the thickness direction. It is possible to arrange each of the first zones so that the adhesive line 29 in the first zone 30 may form four or more layers placed one upon another in the thickness direction.

As illustrated by FIG. 7, a quantity of adhesives B1 in the first zone 30 is larger than a quantity of adhesives B1 in the second zone 31 and adhesives B1 is correspondingly thicker in the first zone 30 than in the second zone 31, so the first and second zones 30, 31 form ups and downs repeated in the longitudinal direction. In the first zone 30 containing the relatively large quantity of adhesives B1, adhesives B1 seep in fibrous interstices of the nonwoven fabric layers 10, 13, 17 more deeply than in the second zone 31 and spreads over the surfaces of the film layers 12, 22 more widely than in the second zone 31. In the second zone 31 containing the relatively small quantity of adhesives B1, on the contrary, the quantity of adhesives B1 seeping in the fibrous interstices of the nonwoven fabric layers 10, 13, 17 as well as the quantity of adhesives B1 spreading over the film layers 12, 22 is correspondingly limited. In the first zones 30, an anchoring effect is more significant than in the second zones 31 and contributes to improvement in an adhesive strength between the nonwoven fabric layers 10, 17, between the nonwoven fabric layers 10, 13 and the film layers 12, 22' as well as in an adhesive strength of the core 4 to the nonwoven fabric layer 10 and the film layer 12. In the second zones 31, stiffness of the nonwoven fabric layers 10, 13, 17 and the film layers 12, 22 is scarcely affected by adhesives B1 even, after adhesives B1 has been cured, so flexibility intrinsic to the nonwoven fabric layers themselves 10, 13, 17 and the film layers themselves 12, 22 can be maintained.

The quantity of adhesives B1 per unit length in the first zone 30 is in a range of 0.0001 to 0.0045 g/cm and the quantity of adhesives B1 per unit length in the second zone 31 is in a range of 0.00003 to 0.0008 g/cm. The quantity of adhesives B1 per unit length in the first zone 30 is three or more times larger than the quantity of adhesives B1 per unit length in the second zone 31.

If the quantity of adhesives B1 in the first zone 30 is less than 0.0001 g/cm, the adhesive strength between the nonwoven fabric layers 10, 17, between the nonwoven fabric layers 10, 13 and the film layers 12, 22 and the adhesive strength of the core 4 to the nonwoven fabric layer 10 and the film layer 12 will be deteriorated. This will lead to the likelihood that the nonwoven fabric layers 10, 17 might peel off from each other and/or the nonwoven fabric layers 10, 13 might peel off from the film layers 12, 22 and/or the core 4 might peel off from the nonwoven fabric layer 10 and the film layer 12. If the quantity of adhesives B1 in the first zone 30 exceeds 0.0045 g/cm, on the contrary, adhesives B1 in the first zone 30 will excessively seep in the fibrous interstices of the nonwoven fabric layers 10, 13, 17 in the thickness direction and/or adhesives B1 will excessively spread over the film layers 12, 22. This will lead to the likelihood that cured adhesives B1 might increase stiffness of the nonwoven fabric layers 10, 13, 17 and the film layers 12, 22 and deteriorate the desired flexibility of the nonwoven fabric layers 10, 13, 17 and the film layers 12, 22.

If the quantity of adhesives B1 in the second zone 31 is less than 0.00003 g/cm, it will be difficult for adhesives B1 in the second zone 31 to join the nonwoven fabric layers 10, 17 to each other and/or to join the nonwoven fabric layers 10, 13 to the film layers 12, 22. As a result, there is anxiety that the second zones 31 might be ineffective to join the nonwoven fabric layers 10, 17 to each other and/or to join the nonwoven fabric layers 10, 13 to the film layers 12, 22. Furthermore, a plurality of ups and downs on the surface of the core 4 will make it impossible to bring adhesives B1 (11, 14) in the second zones 31 in contact with the surface of the core 4 and thereby to join the core 4 to the nonwoven fabric layer 10 and the film layer 12. If the quantity of adhesives B1 in the second zone 31 exceeds 0.0008 g/cm, on the contrary, cured adhesives B1 will increase stiffness of the nonwoven fabric layers 10, 13, 17 and the film layers 12, 22 and consequently deteriorate the flexibility of the nonwoven fabric layers 10, 13, 17 and the film layers 12, 22. The quantities of adhesives per unit length in the first and second zones 30, 31 were measured by a method as follows:

(1) At least one of the topsheet 2, the backsheet 3 and the leak-barrier sheets 16 each including the adhesive lines 29 is separated from the diaper 1 and cut to prepare sheet strips for adhesive content measurement having a length of 1 cm. Each of these sheet strips is weighed by a direct-reading balance. The sheet strip should include a single adhesive line 29.

(2) Adhesives B1 coated on this sheet strip is dissolved in toluene. Process for dissolution of adhesives B1 comprises the following steps. The sheet strip is immersed in toluene for 30 min and then stirred four times at 10 min intervals. After 30 min of immersion, the sheet strip is taken out from toluene and wiped with a filter paper to remove toluene. The sheet strip is immersed again in washing toluene and stirred for 5 min, then taken out from washing toluene and wiped with a filter paper to remove cleaning toluene. Then the sheet strip is dried in an oven (40° C. at full gate opening) for 1 hour and the sheet strip dried in this manner is weighed by the direct-reading balance.

(3) The quantity of adhesives B1 (unit: g/cm) is calculated from an equation $C=(A-B)$, where A represents a weight (unit: g) of the sheet strip before dissolution of adhesives B1, B represents a weight (unit: g) of the sheet strip after dissolution of adhesives B1 and C represents a quantity of adhesives B1 (unit: g/cm) initially coated on the sheet strip.

Along each of the adhesive lines 29, the first-zone 30 has a length T1 in a range of 1 to 10 mm and the second zone 31 has a length T2 in a range of 0.5 to 80 mm. If the length T1 of the first zone 30 is less than 1 mm, the adhesive strength between the nonwoven fabric layers 10, 17, between the nonwoven fabric layers 10, 17 and the film layers 12, 22 and the adhesive strength of the core 4 to the nonwoven fabric layer 10 and the film layer 12 in the first zone 30 will be deteriorated. This may lead to the anxiety, in the first zone 30, that the nonwoven fabric layers 10, 17 might peel off from each other and/or the nonwoven fabric flayers 10, 13 might peel off from the film layers 12, 22 and/or the core 4 might peel off from the nonwoven fabric layer 10 and the film layer 12. If the length T1 of the first zone 30 exceeds 10 mm, on the contrary, cured adhesives B1 will increase stiffness of the nonwoven fabric layers 10, 13, 17 as well as the film layers 12, 22 and correspondingly deteriorate flexibility of the nonwoven fabric layers 10, 13, 17 and the film layers 12, 22. If the length T2 of the second zone 31 exceeds 80 mm, a total area occupied by the first zones 30 in the respective adhesive lines 29 will decrease and correspondingly deteriorate the adhesive strength between the nonwoven fabric layers 10, 17, between the nonwoven fabric layers 10, 13 and the film layers 12, 22 and the adhesive strength of the core 4 to the nonwoven fabric layer 10 and the film layer 12. This may lead to the anxiety that the nonwoven fabric layers 10, 17 might peel off from each other and/or the nonwoven fabric layers 10, 13 might peel off from the film layers 12, 22 and/or the core 4 might peel off from the nonwoven fabric layer 10 and the film layer 12.

Along each of the adhesive lines 29, the first zone 30 has a width T3 in a range of 0.01 to 3 mm and the second zone 31 has a width T4 in a range of 0.003 to 0.5 mm. The width T3 of the first zone 30 is threefold or larger than the width T4 of the second zone 31.

If the width T3 of the first zone 30 is less than 0.01 mm, the effective adhesive areas of the nonwoven fabric layers 10, 13, 17 and those of the film layers 12, 22 in the first zones 30 will be unacceptably limited. The adhesive strength between the nonwoven fabric layers 10, 17, between the nonwoven fabric layers 10, 13 and the film layers 12, 22 and the adhesive strength of the core 4 to the nonwoven fabric layer 10 and the film layer 12 in the first zone 30 will be correspondingly deteriorated. This may lead to the anxiety, in the first zone 30, that the nonwoven fabric layers 10, 17 might peel off from each other and/or the nonwoven fabric layers 10, 13 might peel off from the film layers 12, 22 and/or the core 4 might peel off from the nonwoven fabric layer 10 and the film layer 12. If the width T3 of the first zone 30 exceeds 3 mm, on the contrary, cured adhesives B1 will increase stiffness of the nonwoven fabric layers 10, 13, 17 and the film layers 12, 22 and correspondingly deteriorate flexibility of the nonwoven fabric layers 10, 13, 17 and the film layers 12, 22. If the width T4 of the second zone 31 is less than 0.003 mm, it will be difficult, in the second zone 31, to join the nonwoven fabric layers 10, 17 to each other and to and/or to join the nonwoven fabric layers 10, 13 to the film layers 12, 22. As a result, there is anxiety that the second zones 31 might be ineffective to join the nonwoven fabric layers 10, 17 to each other and/or to join these nonwoven fabric layers 10, 13 to the film layers 12, 22. There is an additional anxiety that adhesives B1 (11, 14) coated on the second zone 31 could not be brought into contact with the surface of the core 4 and the core 4 could be joined neither to the nonwoven fabric layer 10 nor to the film layer 12. The length T1, T2 as well as the width T3, T4 of the first and second zones 30, 31 may be measured by use of magnifying lens or microscope.

Spread per unit area of adhesives B1 on the nonwoven fabric layers 10, 13, 17 and the film layers 12, 22 is in a range of 2.0 to 100 g/m$^2$. The term "spread" used herein refers to the basis weight per unit area (g/m$^2$) of the nonwoven fabric layers 10, 13, 17 and the film layers 12, 22 and is distinguished from the quantity (g/cm) of adhesives B1 per unit length along the adhesive line 29.

If the spread of adhesives B1 on the nonwoven fabric layers 10, 13, 17 and the film layers 12, 22 is less than 2.0 g/m$^2$, the spread of adhesives B1 per unit area will be unacceptably reduced and it will be impossible to join the nonwoven fabric layers 10, 17 to each other and/or to join the nonwoven fabric layers 10, 13 to the film layers 12, 22 and/or to join the core 4 to the nonwoven fabric layer 10 and to the film layer 12. If the spread of adhesives B1 on the nonwoven fabric layers 10, 13, 17 and the film layers 12, 22 exceeds 100 g/m$^2$, cured adhesives B1 will unacceptably increase stiffness of the nonwoven fabric layers 10, 13, 17 and film layers 12, 22 and correspondingly deteriorate flexibility of the nonwoven fabric layers 10, 13, 17 and film layers 12, 22. The spread of adhesives B1 was measured by a method as follows:

(1) At least one of the topsheet 2, the backsheet 3 and the leak-barrier sheets 16 is separated from the diaper 1 and cut to prepare sheet strips for spread measurement of 100 mm×100 mm for adhesive spread measurement. Each of these sheet strips is weighed by a direct-reading balance.

(2) Adhesives B1 coated on the sheet strip is dissolved in toluene. Process for dissolution of adhesives B1 comprises following steps. The sheet strip is immersed in toluene for 30 min and then stirred four times at 10 min intervals. After 30 min of immersion, the sheet strip is taken out from toluene and wiped with a filter paper to remove toluene. The sheet strip is immersed again in washing toluene and stirred for 5 min, then taken out from washing toluene and wiped with a filter paper to remove cleaning toluene. Then the sheet strip is dried in an oven (40° C. at full gate opening) for 1 hour and the sheet strip dried in this manner is weighed by the direct-reading balance.

(3) The spread of adhesives B1 are calculated from an equation $F=(D-E)\div 0.01$, where F represents a spread (g/m$^2$) of adhesives B1, D represents a weight (g) of the sheet strip before dissolution of adhesives B1 and E represents a weight of the sheet strip after dissolution of adhesives B1.

The nonwoven fabric layer 10 defining the topsheet 2 and the nonwoven fabric layer 13 defining the backsheet 3 preferably have a compressibility of 0.3 g·cm/m$^2$ or higher and a thickness not less than 0.2 mm. The nonwoven fabric layers 10, 13 respectively having the compressibility of 0.3 g·cm/m$^2$ or higher and the thickness not less than 0.2 mm advantageously present appropriate bulkiness and flexibility to achieve a comfortable touch when the article is put on a wearer. Even when the nonwoven fabric layers 10, 13 having such compressibility and thickness are used to implement the invention, adhesives B1 (11, 15) deeply seep into the fibrous interstices of the nonwoven fabric layers 10, 13 in the first zones 30 along the respective adhesive lines 29 so that the relatively bulky nonwoven fabric layers 10, 13 can be reliably joined to the film layer 12.

The elastically stretchable sheet 20 preferably has a compressibility of 0.3 g·cm/m$^2$ or higher and a thickness not less than 0.2 mm. The elastically stretchable sheet 20 having the compressibility of 0.3 g·cm/m$^2$ and the thickness not less than 0.2 mm advantageously present appropriate bulkiness and flexibility to achieves comfortable touch when the article is put on a wearer. Even when the elastically stretchable sheet 20 having such compressibility and thickness is used to implement the invention, adhesives B1 (23) deeply seep into the fibrous interstices of the nonwoven fabric layer 22 defining the elastically stretchable sheet 20 in the first zones 30 along the respective adhesive lines 29 so that the relatively bulky stretchable sheet 20 can be reliably joined to the film layer 12. It should be understood that the present invention can be exploited by use of the fabric layers 10, 13 as well as the stretchable sheet 20 having a compressibility lower than 0.3 g·cm/m$^2$ and a thickness less than 0.2 mm. The compressibility and the thickness of the nonwoven fabric layers 10, 13 and the elastically stretchable sheet 20 were measured by a method as follows:

(1) The topsheet 2, the backsheet 3, the leak-barrier sheets 16 and the elastically stretchable sheets 20 are separated from the diaper 1 and then the film layers 12, 22 are separated from the backsheet 2 and the elastically stretchable sheets 20. The sheets 2, 3, 16, 20 are cut to prepare 10 mm×10 mm sheet strips for compressibility measurement and for thickness measurement.

(2) Compressibility is measured using COMPRESSION TESTER (Model KES-FB3 AUTO-A manufactured by KATO TECH CO., LTD. in Japan) is used as the compressibility measuring instrument under conditions as follow: SENS: 2×5, speed: 50 sec/mm, pressurized area: 2 cm$^2$, stroke selected: 5 mm/10 V, maximum load (Fm): 50 gf/cm, and Fm set dial: 5.

(3) Thickness is measured using THICKNESS GAGE (Model UF-60 manufactured by DAIEI KAGAKU SEIKI MFG. CO., LTD. in Japan) under conditions as follow: measuring range: Ø44 mm and measuring pressure: 3 g/cm$^2$. Specifically, the sheet strip is held between jaws of the measuring instrument to read a thickness value. Such measurement is repeated at least 10 times and an average of the measured values is used as the thickness of the relevant sheet.

In the diaper 1, the nonwoven fabric layers 10, 13, 17 and the film layers 12, 22 constituting the top- and backsheets 2, 3, the leak-barrier sheets 16, the elastically stretchable sheets 20 and the core 4 are joined one to another by means of the plural adhesive lines 29 continuously extending in the longitudinal direction. Along each of these adhesive lines 29, the first zones 30 and the second zones 31 alternately extend so that the quantity of adhesives B1 is larger in the first zone 30 than in the second zone 31. The first zones 30 coated with the relatively large quantity of adhesives B1 allow the nonwoven fabric layers 10, 17 to be reliably joined to each other, allow the nonwoven fabric layers 10, 13 to be reliably joined to the film layers 12, 22 and allow the core 4 to be reliably joined to the film layer 12 without the anxiety that these layers might unintentionally peel off one from another.

Each of the adhesive lines 29 comprises the first zones 30 coated with relatively large quantity of adhesives B1 and the second zones 31 coated with relatively small quantity of adhesives B1. Compared to the case in which the adhesive line 29 exclusively comprises the first zones 30, the diaper 1 according to the invention allows the flexibility which is intrinsic to the nonwoven fabric layers 10, 13, 17 as well as the film layers 12, 22 to be maintained. In this diaper 1, the adhesive lines 29 serve to join the nonwoven fabric layers 10, 13, 17, the film layers 12, 22 and the core 4 one to another and thereby to prevent the nonwoven fabric layers 10, 13, 17 as well as the film layers 12, 22 and the core 4 from unintentionally peeling off one from another without deteriorating the flexibility which is intrinsic to the nonwoven fabric layers 10, 13, 17 and the film layers 12, 22.

Figure 8:
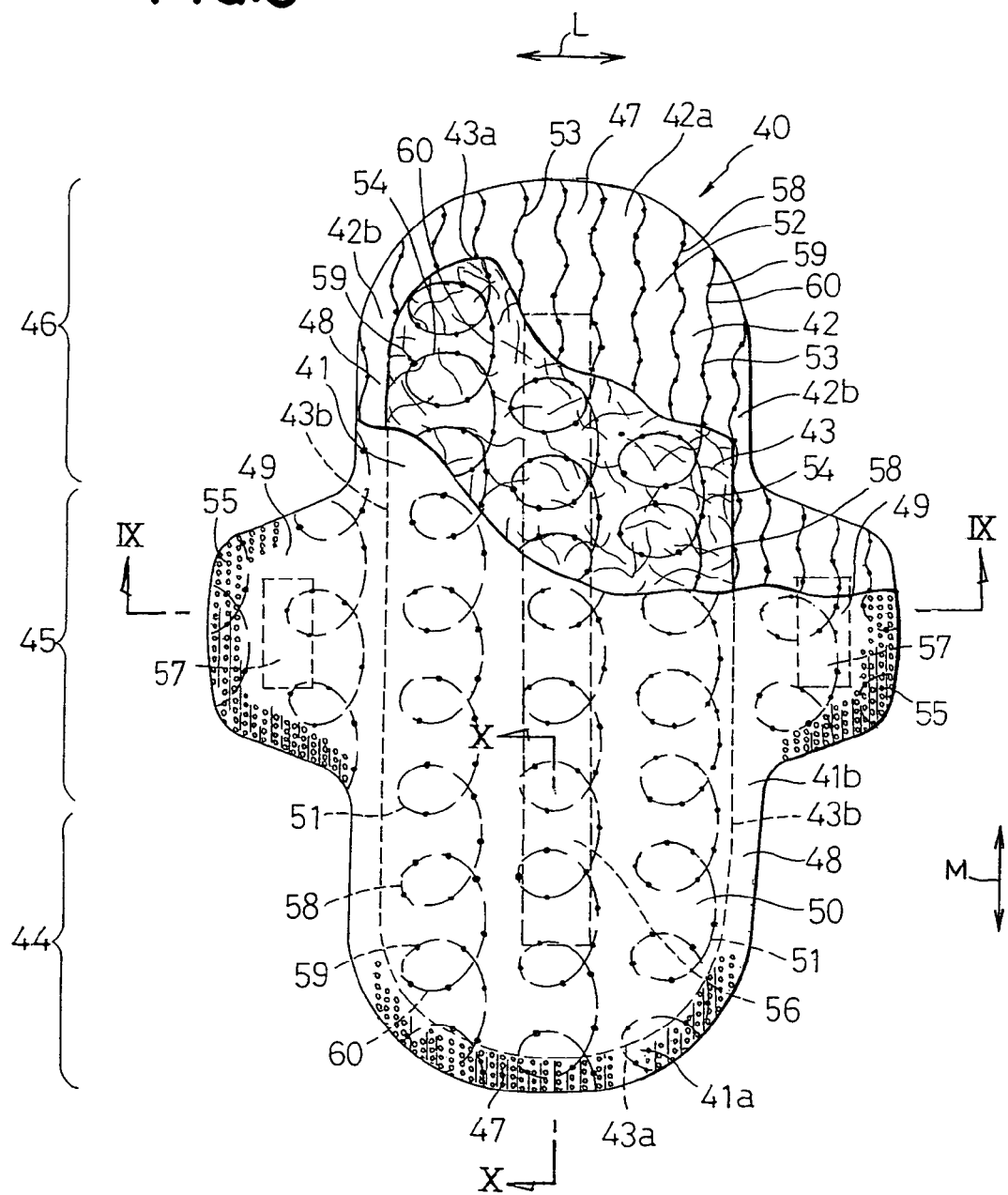
FIG. 8 is a partially cutaway perspective view depicting a sanitary napkin as another embodiment of the invention.
Figure 9:
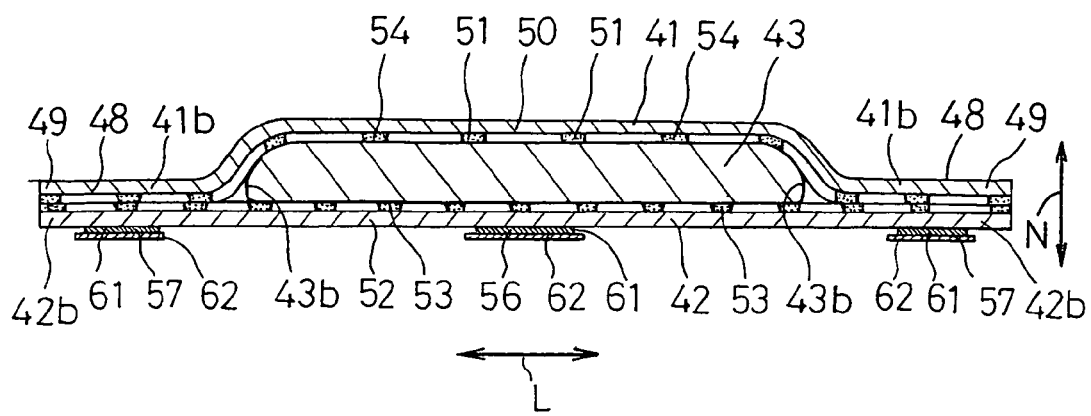
FIG. 9 is a sectional view taken along the line IX—IX in FIG. 8.
Figure 10:
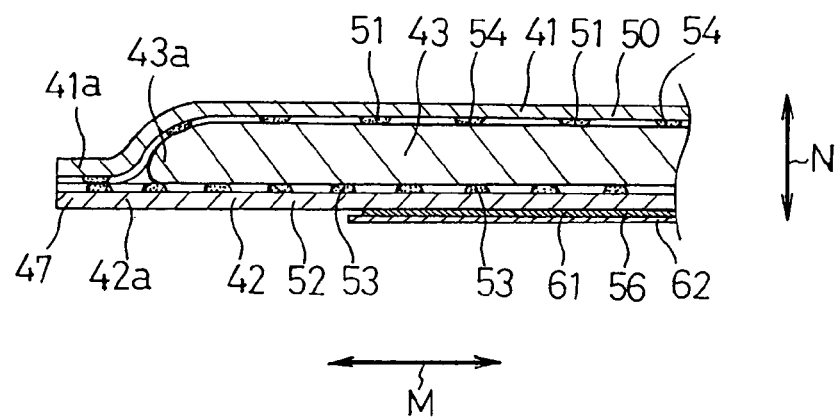
FIG. 10 is a sectional view taken along the line X—X in FIG. 8.

FIG. 8 is a partially cutaway perspective view depicting a sanitary napkin 40 as another embodiment of the invention, FIG. 9 is a sectional view taken along the line IX—IX in FIG. 8, FIG. 10 is a sectional view taken along the line X—X in FIG. 8 and FIG. 11 is a partial overhead view depicting nonwoven fabric 50 and film 52 joined together by means of adhesives 51, 53. More specifically, FIG. 11 illustrates the state in which the nonwoven fabric 50 and the film 52 joined together by means of adhesives 51, 53 have been compressed in the thickness direction. In FIGS. 8, 9, 10 and 11, the transverse direction is indicated by an arrow L (only in FIGS. 8 and 9), the longitudinal direction is indicated by an arrow M (only in FIGS. 8 and 10) and the thickness direction is indicated by an arrow N (only in FIGS. 9 and 10).

The napkin 40 basically comprises a liquid-pervious topsheet 41 lying on the skin-contactable side, a liquid-impervious backsheet 42 lying on the non-skin-contactable side, and a liquid-absorbent core 43 interposed between the top- and backsheets 41, 42. The napkin 40 is composed of, as viewed in a longitudinal direction, a front region 44, a rear region 46 and an intermediate region 45 extending between the two regions 44, 46. The napkin 40 further comprises longitudinally opposite end zones 47 extending in a transverse direction outside longitudinally opposite ends 43a of the core 43 and transversely opposite lateral marginal zones 48 extending in the longitudinal direction outside transversely opposite side edges 43b of the core 43. The core 43 is similar to that in the diaper 1 of FIG. 1 and extending primarily over the intermediate region 45 further into the front and rear regions 44, 46 so as to occupy transversely middle zones of the regions 44, 45, 46. The lateral marginal zones 48 of the intermediate region 45 are formed with a pair of wings 49 extending outward in the transverse direction.

The topsheet 41 is formed from a hydrophilic fibrous nonwoven fabric 50 and having longitudinally opposite end zones 41a extending outward beyond the ends 43a of the core 43 in the longitudinal direction and transversely opposite lateral marginal zones 41b extending outward beyond the side edges 43b of the core 43. The nonwoven fabric 50 is coated on its inner surface with a plurality of curved adhesive lines 51 continuously extending in the longitudinal direction. The backsheet 42 is formed from a plastic film 52 and has longitudinally opposite end zones 42a extending in the longitudinal direction outward beyond the ends 43a of the core 43 and transversely opposite lateral marginal zones 42b extending in the transverse direction outward beyond the side edges 43b of the core 43. The film 52 is coated on its inner surface with a plurality of curved adhesive lines 53 continuously extending in the longitudinal direction. The nonwoven fabric 13 is coated on its inner surface with a plurality of adhesive lines 15 continuously extending in the longitudinal direction. The core 43 is coated on its upper surface with a plurality of curved adhesive lines 54 extending in the longitudinal direction. In the end zones 41a, 42a and the lateral marginal zones 41b, 42b of the top- and backsheet 41, 42, respectively, the inner surface of the nonwoven fabric 50 and the inner surface of the film 52 are joined to each other by means of adhesives 51, 53. The core 43 is joined to the inner surface of the nonwoven fabric 50 and to the inner surface of the film 52 by means of adhesives 51, 51, 54, respectively. In the end zones 47 and the lateral marginal zones 48, in addition to the adhesives 51, 53, a plurality of dot-pattern heal-sealing spots 55 serve to join the inner surface of the nonwoven fabric layer 50 to the inner surface of the film layer 52.

The napkin 40 is formed in its transversely middle region with adhesive zone 56 extending in the longitudinal direction and on the respective wings 49 with adhesive zones 57 extending in the longitudinal direction. The adhesive zones 56, 57 are formed on the outer surface of the film layer 52. The adhesive zones 56, 57 are coated with pressure-sensitive adhesives 61 which is, in turn, covered with and protected by a release paper 62. To put the napkin 40 on a wearer, the release paper 62 is peeled off from the respective adhesive zones 56, 57, the adhesive zone 56 is anchored on the inner side of a wearer's shorts and the wings 49 are folded back onto the outer side of the shorts so that the wings 49 may be anchored on the outer side of the shorts by means of the adhesive zone 57.

Adhesives 51, 54 coated on the nonwoven fabric layer 50 defining the topsheet 41 and on the core 43, respectively, form a plurality of independent adhesive lines 58 continuously extending in the longitudinal direction, describing spiral patterns. Adhesives 53 coated on the film layer 52 defining the backsheet 42 form a plurality of independent adhesive lines 58 continuously extending in the longitudinal direction in zigzag patterns. Of these adhesive lines 58, each pair of the adjacent lines 58 do not intersect each other and are spaced from each other by a predetermined dimension in the transverse direction. Each of the lines 58 comprises first zones 59 and second zones 60 arranged alternately in the longitudinal direction. In each of the first zones 59, the adhesive line 58 forms three layers placed one upon another in the thickness direction (See FIG. 6). It is possible to arrange each of the first zones 59 so that the adhesive line 58 in the first zone 59 may form four or more layers placed one upon another in the thickness direction.

In the adhesive lines 58, a quantity of adhesives 51, 53, 54 (referred to hereinafter as adhesives B2) in the first zone 59 is larger than a quantity of adhesives B2 in the second zone 60. In the first zone 59 containing the relatively large quantity of adhesives B2, adhesives B2 (51, 54) seeps in fibrous interstices of the nonwoven fabric layer 50 more deeply than in the second zone 60 and adhesives B2 (53) spreads over the surface of the film layer 52 more widely than in the second zone 60. In the second zone 60 containing the relatively small quantity of adhesives B2, on the contrary, the quantity of adhesives B2 (51, 54) seeping in the fibrous interstices of the nonwoven fabric layer 50 as well as the quantity of adhesives B2 spreading over the film layer 52 is correspondingly limited. In the first zones 59, an anchoring effect is more significant than in the second zones 60 and contributes to improvement in an adhesive strength between the nonwoven fabric layer 50 and the film layer 52 and an adhesive strength of the core 43 to the nonwoven fabric layer 50 and to the film layer 52. In the second zones 60, stiffness of the nonwoven fabric layer 50 and the film layer 52 is scarcely affected by adhesives B2 even after adhesives B2 has been cured, so flexibility intrinsic to the nonwoven fabric layer 50 and the film layer 52 can be maintained.

The quantity of adhesives B2 per unit length in the first zone 59 is in a range of 0.0001 to 0.0045 g/cm and the quantity of adhesives B2 per unit length in the second zone 60 is in a range of 0.00003 to 0.0008 g/cm. The quantity of adhesives B2 per unit length in the first zone 59 is three or more times larger than the quantity of adhesives B2 per unit length in the second zone 60.

If the quantity of adhesives B2 in the first zone 59 is less than 0.0001 g/cm, it is likely that the nonwoven fabric layer 50 and the film layer 52 might peel off from each other in the first zone 59 and the core 43 might peel off from the nonwoven fabric layer 52 and the film layer 52 in the first zone 59. If the quantity of adhesives B2 in the first zone 59 exceeds 0.0045 g/cm, on the contrary, adhesives B2 (51, 54) in the first zone 59 will excessively seep in the fibrous interstices of the nonwoven fabric layer 50 in the thickness direction and/or adhesives B2 (53) will excessively spread over the film layer 52. This will lead to the likelihood that cured adhesives B2 might increase stiffness of the nonwoven fabric layer 50 as well as of the film layer 52 and deteriorate the desired flexibility of the nonwoven fabric layer 50 and the film layer 52. If the quantity of adhesives. B2 in the second zone 59 is less than 0.00003 g/cm, it will be difficult for adhesives B2 in the second zone 60 to bond the nonwoven fabric layer 50 to the film layer 52. Furthermore, a plurality of ups and downs on the surface of the core 43 will make it impossible to bring adhesives B2 (51, 53) in the second zones 31 in contact with the surface of the core 43 and thereby to join the core 43 to the nonwoven fabric layer 50 and the film layer 52. If the quantity of adhesives B2 in the second zone 60 exceeds 0.0008 g/cm, on the contrary, cured adhesives B2 will increase stiffness of the nonwoven fabric layer 50 and the film layer 52 and consequently deteriorate the flexibility of the nonwoven fabric layer 50 and the film layer 52.

Along each of the adhesive lines 58, the first zone 59 has a length T1 in a range of 1 to 10 mm and the second zone 60 has a length T2 in a range of 0.5 to 80 mm. If the length T1 of the first zone 59 is less than 1 mm, there is anxiety, in the first zone 59, that the nonwoven fabric layer 50 and film layer 52 might peel off from each other and/or the core 43 might peel off from the nonwoven fabric layer 50 and the film layer 52. If the length T1 of the first zone 30 exceeds 10 mm, on the contrary, cured adhesives B2 will increase stiffness of the nonwoven fabric layer 50 as well as the film layer 52 and correspondingly deteriorate flexibility of the nonwoven fabric layer 50 and the film layer 52. If the length T2 of the second zone 60 exceeds 80 mm, a total area occupied by the first zones 59 in the respective adhesive lines 58 will decrease and correspondingly deteriorate the adhesive strength between the nonwoven fabric layer 50 and the film layer 0.52 and the adhesive strength of the core 43 to the nonwoven fabric layer 50 and the film layer 52. This may lead to the anxiety that the nonwoven fabric layer 50 and the film layer 52 might peel off from each other and/or the nonwoven fabric layers 10, 13 might peel off from the film layers 12, 22 and/or the core 43 might peel off from the nonwoven fabric layer 50 and the film layer 52.

Along each of the adhesive lines 58, the first zone 59 has a width T3 in a range of 0.01 to 3 mm and the second zone 60 has a width T4 in a range of 0.003 to 0.5 mm. The width T3 of the first zone 59 is threefold or larger than the width T4 of the second zone 60.

If the width T3 of the first zone 59 is less than 0.01 mm, the effective adhesive areas of the nonwoven fabric layer 50 and the film layers 52 in the first zones 59 will be unacceptably limited. This may lead to the anxiety, in the first zone 59, that the nonwoven fabric layers 10, 17 might peel off from each other and/or the nonwoven fabric layer 50 and the film layer 52 might peel off from each other and/or the core 43 might peel off from the nonwoven fabric layer 50 and the film layer 52. If the width T3 of the first zone 59 exceeds 3 mm, on the contrary, cured adhesives B2 will increase stiffness of the nonwoven fabric layer 50 and the film layer 52 and correspondingly deteriorate flexibility of the nonwoven fabric layer 50 and the film layer 52. If the width T4 of the second zone 60 is less than 0.003 mm, it will be impossible, in the second zone 60, to join the nonwoven fabric layer 50 and the film layer 52 to each other and/or to join the core 43 to the nonwoven fabric layer 50 and the film layer 52.

Spread per unit area of adhesives B2 on the nonwoven fabric layer 50, the film layer 52 and the core 43 is in a range of 2.0 to 100 g/m$^2$. If the spread of adhesives B2 on the nonwoven fabric layer 50, the film layer 52 and the core 43 is less than 2.0 g/m$^2$, the spread of adhesives B2 per unit area will be unacceptably reduced and it will be impossible to join the nonwoven fabric layer 50 and the film layer 52 to each other and/or to join the core 43 to the nonwoven fabric layer 50 and to the film layer 52. If the spread of adhesives B2 on the nonwoven fabric layers 50 and the film layer 52 exceeds 100 g/m$^2$, cured adhesives B2 will unacceptably increase stiffness of the nonwoven fabric layer 50 and film layer 52 and correspondingly deteriorate flexibility of the nonwoven fabric layer 50 and the film layers 52.

The quantity (g/cm) of adhesives B2 in the first and second zones 59, 60 per unit length, the length (mm) and the width (mm) of the first and second zones 59, 60, and the spread of adhesives B2 (g/m$^2$) may be measured by the same methods as have been described with respect to the diaper 1 of FIG. 1.

The nonwoven fabric layer 50 defining the topsheet 41 preferably have a compressibility of 0.3 g·cm/m$^2$ or higher and a thickness not less than 0.2 mm. The nonwoven fabric layer 50 having the compressibility of 0.3 g·cm/m$^2$ or higher and the thickness not less than 0.2 mm advantageously present an appropriate bulkiness and a flexibility to achieve a comfortable touch when the article is put on a wearer. Even when the nonwoven fabric layer 50 having such compressibility and thickness are used to exploit the invention, adhesives B2 (51) in the first zone 59 of the adhesive line 58 deeply seep into the fibrous interstices of the nonwoven fabric layer 50 so that the relatively bulky nonwoven fabric layer 50 can be reliably joined to the film layer 52. The compressibility (g cm/m$^2$) and the thickness (mm) may be measured by the same methods as have been described with respect to the diaper 1 of FIG. 1.

In the napkin 40, the nonwoven fabric layer 50 and the film layer 52 constituting the top- and backsheets 41, 42 and the core 43 are joined one to another by means of the plural adhesive lines 58 continuously extending in the longitudinal direction. Along each of these adhesive lines 58, the first zones 59 and the second zones 60 alternately extend so that the quantity of adhesives B2 is larger in the first zone 59 than in the second zone 60. The first zones 59 coated with the relatively large quantity of adhesives B2 allow the nonwoven fabric layer 50 and the film layer 52 to be reliably joined to each other and allow the core 43 to be reliably joined to the nonwoven fabric layer 50 and the film layer 12 without the anxiety that these layers 50, 52 and the core 43 might unintentionally peel off one from another. The adhesive lines 58 extend in a spiral or zigzag pattern so that the nonwoven fabric layer 50, the film layer 52 and the core 43 can be joined together with the adhesive strength which is substantially uniform in any one of the longitudinal direction and the transverse direction. Even if a peeling force is exerted on the napkin 40 in these two directions, there is no anxiety that the nonwoven fabric layer 50 and the film layer 52 might peel off from each other and the core 43 might peel off from the nonwoven fabric layer 50 and the film layer 52.

Each of the adhesive lines 58 comprises the second zones 60 coated with a smaller quantity of adhesives B2 than the first zone 59. Compared to the case in which the adhesive line 58 exclusively comprises the first zones 59, the napkin 40 according to the invention allows the flexibility which is intrinsic to the nonwoven fabric layer 50 as well as to the film layer 52 to be maintained. In this napkin 40, the adhesive lines 58 serve to join the nonwoven fabric layer 50, the film layer 52 and the core 43 one to another and thereby to prevent the nonwoven fabric layer 50 as well as the film layer 52 and the core 43 from unintentionally peeling off one from another without deteriorating the flexibility which is intrinsic to these nonwoven fabric layer 50 and the film layer 52.

As a stock material for the topsheet 2, 41, in addition to a hydrophilic fibrous nonwoven fabric, a hydrophobic fibrous nonwoven fabric having a plurality of apertures or finely perforated plastic film. A stock material for the backsheet 3, 42 may be selected from the group consisting of a hydrophobic fibrous nonwoven fabric, a breathable liquid-impervious plastic film and a composite nonwoven fabric comprising a belt blown fibrous nonwoven fabric having a high water-resistance and a spun bond fibrous nonwoven fabric having a high strength and flexibility joined to at least one surface of the melt blown fibrous nonwoven fabric.

The fibrous nonwoven fabric used for exploitation of the present invention may be selected from the group consisting of those obtained by spun lacing-, needle punching-, melt blowing-, thermal bonding-, spun bonding-, and chemical bonding-processes, respectively. The component fiber of the nonwoven fabric may be selected from the group consisting of polyolefin-, polyester- and polyamide-based fibers and core-sheath-type or side-by-side-type conjugate fibers of polyethylene/polypropylene or polyethylene/polyester.

It is possible to form the backsheet using a stock material selected from the group consisting of an elastically stretchable hydrophobic fibrous nonwoven fabric, an elastically stretchable breathable liquid-impervious plastic film and a composite sheet comprising an elastically stretchable hydrophobic fibrous nonwoven fabric and an elastically stretchable breathable liquid-impervious plastic film laminated one upon another. It is also possible to form the backsheet 3 using a composite nonwoven fabric comprising an elastically stretchable hydrophobic fibrous nonwoven fabric and a hydrophobic fibrous nonwoven fabric made of crimped fibers obtained by a melt spinning thermoplastic synthetic resin selected from the group consisting of polypropylene, polyethylene and polyester, the latter laminated upon at least one surface of the former. The elastically stretchable fibrous nonwoven fabric may be selected from the group consisting of those obtained by a melt blowing process and a spun bonding process. As the component fibers of the elastic stretchable nonwoven fabric, elastically stretchable fibers made of a melt spinning suitable thermoplastic elastomer resin may be used.

Adhesives B1, B2 may be selected from the group consisting of hot melt adhesives, acrylic adhesives and elastomeric adhesive.

In the diaper 1 of FIG. 1, it is possible to coat the core 4 with adhesives in a manner that a plurality of substantially rectilinear adhesive lines 29 continuously extending independently of one another in the longitudinal direction on the core 4. It is also possible to provide the substantially rectilinear adhesive lines 29 either in the transverse direction or in both the longitudinal and transverse directions. Furthermore, it is possible to provide these adhesive lines 29 extending in a spiral or zigzag pattern as in the napkin 40 of FIG. 8. The diaper 1 is not limited to the open-type diaper but may be of the pants-type in which the side flaps 9 in the front and rear waist regions 5, 7 are previously connected with each other. In the napkin 40 of FIG. 8, it is possible to provide the substantially rectilinear adhesive lines 58 extending in any one of the longitudinal direction and the transverse direction or in both the longitudinal and transverse directions. The disposable wearing article is not limited to the diaper 1 and the napkin 40 but includes a urine pad and a mother's milk pad.

The disposable wearing article according to the present invention is primarily characterized in that a plurality of adhesive lines continuously extending in a given direction each having first and second zones arranged alternately along the adhesive line serve to join the sheets to each other and to join the liquid-absorbent core to these sheets. In the first zones containing much more quantity of adhesives than the second zones, the sheets can be reliably joined to each other and the core can be reliably joined to the sheets without the anxiety that the sheets might peel off from each other and the core might peel off from the sheets. In contrast with the case in which the adhesive-lines comprise only the first zones, the second zones containing relatively small quantity of adhesives serve to prevent the cured adhesives from deteriorating the desired flexibility of the sheets and thereby to maintain the flexibility intrinsic to the sheets. In this way, it is simultaneously ensured that peeling off between the sheets as well as between the sheets and the core can be reliably avoided and the desired flexibility of the sheets can be reliably maintained.

Even when the sheets are formed from a fibrous nonwoven fabric layer and/or a plastic film layer, adhesives in the first zones deeply seep in fibrous interstices of the nonwoven fabric and widely spread over the film. In consequence, the adhesive strength between the nonwoven fabric layers, between the nonwoven fabric layer and the film layer and the adhesive strength of the core to the nonwoven fabric layer and the film layer can be enhanced to eliminate the anxiety that the nonwoven fabric layers might peel off from each other and/or the nonwoven fabric layer and the film might peel off from each other and/or the core might peel off from the nonwoven fabric layer and the film layer. A quantity of adhesives in the second zones possibly seeping into the fibrous interstices of the nonwoven fabric layer is of a negligible degree and a range that adhesives in the second zones possibly spreads over the film layer is limited. In the second zones, therefore, both the nonwoven fabric layer and the film are not affected by cured adhesives and the flexibility intrinsic to the nonwoven fabric layer and the film can be reliably maintained.

The wearing article according to the invention allows a flexible and soft touch of the sheet which is contactable with a wearer to be maintained and, in addition, there is unlikely that the sheets might peel off from each other and the core might peel off from the sheet even if the movement of a wearer is transmitted to the article. From these viewpoints, the present invention is suitably applicable to disposable diapers and sanitary napkins.

What is claimed is:

1. A disposable wearing article, comprising:
   at least a pair of sheets;
   a liquid-absorbent core interposed between said sheets;
   adhesive lines permanently bonding at least two of said core and said sheets together; and
   elastic members bonded to at least one of said sheets along peripheral edges of a waist hole and leg holes of said article;
   wherein
   said at least two of said core and said sheets are bonded together by said adhesive lines in regions free of said elastic members;
   said adhesive lines are applied on at least one surface of at least one of said core and said sheets and continuously extend in a given direction, each of said adhesive lines having first zones and second zones alternately arranged along the adhesive line;
   each of said first zones contains a greater amount of adhesive material or has a greater thickness of said adhesive material than each of said second zones;
   said first zones are distributed along the respective adhesive lines at regular intervals;
   a quantity of said adhesive material per unit length of said first zones is in a range of 0.0001 to 0.0045 g/cm and a quantity of said adhesive material per unit length of said second zones is in a range of 0.00003 to 0.0008 g/cm; and
   the quantity of said adhesive material per unit length of said first zones is three or more times larger than the quantity of said adhesive material per unit length of said second zones.

2. A disposable wearing article, comprising:
   at least a pair of sheets;
   a liquid-absorbent core interposed between said sheets;
   elastic members directly bonded to at least one of said sheets and along peripheral edges of a waist hole and leg holes of said article; and
   adhesive lines some of which are disposed between and directly bond the elastic members to said at least one of said sheets, the remaining adhesive lines being disposed between and permanently and directly bonding at least two of said core and said sheets together without directly bonding the elastic members to any of said core and sheets;
   said adhesive lines continuously extending in a given direction, each of said adhesive lines having first zones and second zones alternately arranged along the adhesive line;
   wherein
   each of said first zones contains a greater amount of adhesive material or has a greater thickness of said adhesive material than each of said second zones;
   said first zones are distributed along the respective adhesive lines at regular intervals; and
   each of said first zones includes at least three layers of said adhesive material placed one upon another in a thickness direction of said article and each of said second zones includes a single layer of said adhesive material.

3. The article of claim 2, wherein all said adhesive lines are elongated in a longitudinal direction of said article and extend transversely of the elastic members bonded along the peripheral edge of the waist hole of said article.

4. A disposable wearing article, comprising:
   at least a pair of sheets;
   a liquid-absorbent core interposed between said sheets;
   adhesive lines permanently bonding at least two of said core and said sheets together; and
   elastic members directly bonded to a surface of at least one of said sheets and along peripheral edges of a waist hole and leg holes of said article;
   wherein
   said at least two of said core and said sheets are bonded together by said adhesive lines at surfaces that are not directly bonded to said elastic members, said adhesive lines being applied on at least one of said surfaces and continuously extending in a given direction, each of said adhesive lines having first zones and second zones alternately arranged along the adhesive line;

each of said first zones contains a greater amount of adhesive material or has a greater thickness of said adhesive material than each of said second zones;
said first zones are distributed along the respective adhesive lines at regular intervals;
a width of each said first zone, as measured in a direction transverse to said given direction, is in a range of 0.01 to 3 mm and a width of each said second zone, as measured in the direction transverse to said given direction, is in a range of 0.003 to 0.5 mm; and
the width of each said first zone is three or more times greater than the width of each said second zone.

* * * * *